United States Patent
Hofmann et al.

[11] Patent Number: 5,605,669
[45] Date of Patent: Feb. 25, 1997

[54] PROCESS OF PREPARING CESIUM SALTS FROM CESIUM ALUMINUM ALUM

[75] Inventors: Hartmut Hofmann, Bad Soden; Klaus Köbele, Dietzenbach; Horst Prinz, Friedberg; Bernd Phillipp, Langelsheim; Gerd Harms, Goslar; Alexander Schiedt, Mainz; Ulrike Hecktor, Friedberg, all of Germany

[73] Assignee: Metallgesellschaft Aktiengesellschaft, Frankfurt am Main, Germany

[21] Appl. No.: 537,927

[22] PCT Filed: Apr. 19, 1994

[86] PCT No.: PCT/EP94/01202

§ 371 Date: Nov. 24, 1995

§ 102(e) Date: Nov. 24, 1995

[87] PCT Pub. No.: WO94/25422

PCT Pub. Date: Nov. 10, 1994

[30] Foreign Application Priority Data

Apr. 24, 1993 [DE] Germany .......................... 43 13 480.7

[51] Int. Cl.$^6$ .............................. C22B 26/10; C01D 3/00; C01F 1/00; C07C 55/00
[52] U.S. Cl. ...................... 423/208; 423/499.1; 423/127; 423/166; 562/590; 562/607; 562/609
[58] Field of Search ................... 423/202, 208, 423/127, 499.1, 166; 562/590, 607, 609

[56] References Cited

U.S. PATENT DOCUMENTS

| | | | |
|---|---|---|---|
| 2,481,455 | 9/1949 | Stenger | 423/499.1 |
| 3,130,010 | 4/1964 | Moolenaar et al. | 562/590 |
| 3,207,571 | 9/1965 | Berthold . | |
| 3,489,509 | 1/1970 | Johnson | 562/607 |

FOREIGN PATENT DOCUMENTS

| | | | |
|---|---|---|---|
| 1253252 | 11/1967 | Germany . | |
| 949483 | 2/1964 | United Kingdom | 423/208 |

*Primary Examiner*—Steven Bos
*Attorney, Agent, or Firm*—Michael J. Striker

[57] ABSTRACT

This invention relates to the preparation of cesium salts from cesium-aluminum-alum in a process in which the cesium-aluminum-alum is reacted in a single vessel in the presence of water with calcium hydroxide in an amount which is equimolar to the amount of aluminum and with a readily water-soluble calcium salt in an amount which is equimolar to the amount of cesium and the precipitated aluminum hydroxide and the precipitated calcium sulfate are separated by filtration or centrifugation.

7 Claims, No Drawings

PROCESS OF PREPARING CESIUM SALTS FROM CESIUM ALUMINUM ALUM

BACKGROUND OF THE INVENTION

This invention relates to a process of preparing cesium salts from cesium-aluminum-alum.

U.S. Pat. No. 3,489,509 discloses a process of preparing cesium compounds having a high purity. Cesium-alu-minum-alum is treated with barium hydroxide and is subsequently reacted with carbon dioxide. Thereafter barium halide is added in a stoichiometric amount so that pure cesium halide is formed. For the formation of cesium halide from cesium-aluminum-alum it is undesirable that the use of barium hydroxide and barium halides involves substantial costs and that a neutralization must be effected by a reaction with carbon dioxide.

SUMMARY OF THE INVENTION

It is an object of the invention to provide a process by which the disadvantages described hereinbefore can be avoided.

That object is accomplished in accordance with the invention in that cesium-aluminum-alum is reacted in a single vessel in the presence of water with calcium hydroxide in an amount which is equimolar to the amount of aluminum and with a readily water-soluble calcium salt in an amount which is equimolar to the amount of cesium and the precipitated aluminum hydroxide and the precipitated calcium sulfate are separated by filtration or centrifugation. In the process in accordance with the invention the use of barium compounds, which are more expensive than calcium compounds, and the neutralization with carbon dioxide are omitted and the further advantage is provided that the direct reaction results in cesium salt solutions in the concentration range of >10%. This considerably reduces the work required to remove water in the preparation of concentrated cesium salt solutions and of solid salts.

Whereas it would be obvious to directly react cesium-aluminum-alum with the stoichiometric amount of calcium hydroxide according to the equation $$CsAl(SO_4)_2 + 2Ca(OH)_2 \rightarrow CsOH + Al(OH)_3 + 2CaSO_4$$

that reaction will not give satisfactory yields of cesium hydroxide, probably because the resulting precipitate of aluminum hydroxide and gypsum masks the surface of suspended calcium hydroxide so that it is not available for the reaction. On the other hand it is not possible to compensate the amount of masked calcium hydroxide by the use of calcium hydroxide in a surplus which can be so exactly controlled that a contamination of the desired product cesium hydroxide with calcium hydroxide, which can be removed only with difficulty, can be avoided. For this reason it is common in the art to use barium hydroxide, which is more readily soluble but is much more expensive.

By the process in accordance with the invention the pure cesium salts can surprisingly be prepared by a reaction in a single vessel. The formate, acetate, citrate, chloride or bromide of calcium, can desirably be used as a readily water-soluble calcium salt.

The cesium salts are preferably prepared from cesium-aluminum-alum in that the reaction is carried out at temperatures in the range from 80° to 120° C. and at a suspension density which at the beginning of the reaction amounts to 100 to 500 g insoluble solids per liter water. The insoluble solids consist of those partial amounts of $Ca(OH)_2$, of the cesium salt, and of the cesium-aluminum-alum which are insoluble at the beginning of the reaction.

The invention will be explained more in detail in the following examples.

EXAMPLE 1

Preparation of Cesium Formate

A heatable and stirrable vessel having a capacity of 500 liters was charged with 290 liters water, 17 kg calcium oxide, and 13 kg calcium formate. The suspension was heated to the boiling point with stirring and then 111 kg cesium-aluminum-alum were added. The reaction mixture was stirred at its boiling point for two hours and was subsequently allowed to cool and was then filtered. The filtrate contained about 11% cesium formate, 0.1% calcium ions, 0.05% aluminum ions, and 1% sulfate ions. The filtration residue was re-washed with water. About 95% of the cesium that had been supplied were converted to cesium formate and were detected in the combined filtrates.

EXAMPLE 2

Preparation of Cesium Acetate

An apparatus which was similar to that used in Example 1 but had a capacity of 1000 liters was charged with 375 liters water, 43.8 kg calcium oxide, and 45.8 kg calcium acetate. The suspension was heated to its boiling point; then 296 kg cesium-aluminum-alum were added. Thereafter the suspension was stirred at its boiling point for 2 hours and was allowed to coot and was then filtered. The resulting solution contained about 20% cesium acetate and contained 58% of the cesium that had been supplied. The filtration residue was re-washed to recover additional 37% of the supplied cesium as an aqueous solution of cesium acetate.

We claim:
1. A process of making a cesium salt from cesium-aluminum-alum, said process comprising the steps of:
   a) reacting cesium-aluminum-alum with calcium hydroxide in an amount equimolar to aluminum in said cesium-aluminum-alum and a water-soluble calcium salt in an amount equimolar to cesium in said cesium-aluminum-alum in the presence of water in a single vessel to precipitate aluminum hydroxide and calcium sulfate; and
   b) separating the aluminum hydroxide and calcium sulfate precipitated in step a) from filtrate which contains the cesium salt by one of filtering and centrifuging.
2. The process as defined in claim 1, wherein said calcium salt is calcium formate.
3. The process as defined in claim 1, wherein said calcium salt is calcium acetate.
4. The process as defined in claim 1, wherein said calcium salt is calcium citrate.
5. The process as defined in claim 1, wherein said calcium salt is calcium chloride.
6. The process as defined in claim 1, wherein said calcium salt is calcium bromide.
7. The process as defined in claim 4, wherein the reacting is performed at a temperature of from 80 to 120° C. and at a suspension density amounting to 100 to 500 g of insoluble solids per liter of said water at a start of the reacting.

* * * * *

UNITED STATES PATENT AND TRADEMARK OFFICE
CERTIFICATE OF CORRECTION

PATENT NO. : 5,605,669
DATED : Feb. 25, 1997
INVENTOR(S) : Hartmut Hofmann, et al.

It is certified that error appears in the above-identified patent and that said Letters Patent is hereby corrected as shown below:

Column 2, line 61, change "claim 4" to --claim 1--.

Signed and Sealed this

Twentieth Day of July, 1999

Attest:

Q. TODD DICKINSON

Attesting Officer

Acting Commissioner of Patents and Trademarks